(12) United States Patent
Cunningham et al.

(10) Patent No.: US 10,605,735 B2
(45) Date of Patent: Mar. 31, 2020

(54) PHOTONIC RESONATOR OUTCOUPLER MICROSCOPY (PROM)

(71) Applicant: The Board of Trustees of the University of Illinois, Urbana, IL (US)

(72) Inventors: Brian T. Cunningham, Champaign, IL (US); Yue Zhuo, Champaign, IL (US); Brendan Harley, Urbana, IL (US); Ji Sun Choi, Urbana, IL (US); Thibault Marin, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/164,302

(22) Filed: Oct. 18, 2018

(65) Prior Publication Data

US 2019/0120766 A1    Apr. 25, 2019

Related U.S. Application Data

(60) Provisional application No. 62/574,877, filed on Oct. 20, 2017.

(51) Int. Cl.
*G01J 3/28*       (2006.01)
*G01N 21/64*      (2006.01)
(Continued)

(52) U.S. Cl.
CPC ......... *G01N 21/648* (2013.01); *G01N 21/255* (2013.01); *G01N 21/27* (2013.01);
(Continued)

(58) Field of Classification Search
CPC .... G01N 21/648; G01N 21/552; G01N 21/27; G01N 21/255; G01N 21/6458;
(Continued)

(56) References Cited

U.S. PATENT DOCUMENTS 7,023,544 B2    4/2006  Cunningham et al.
7,264,973 B2    9/2007  Lin et al.
(Continued)

OTHER PUBLICATIONS

M. E. Berginski et al., "High-resolution quantification of focal adhesion spatiotemporal dynamics in living cells," PLoS One, vol. 6, Issue 7, p. e22025 (Jul. 2011).
(Continued)

*Primary Examiner* — Abdullahi Nur
(74) *Attorney, Agent, or Firm* — McDonnell Boehnen Hulbert & Berghoff LLP

(57) ABSTRACT

Photonic Resonator Outcoupler Microscopy (PROM) is a novel, label-free approach for dynamic, long-term, quantitative imaging of a sample on a surface of a photonic crystal (PC) biosensor, in which components of the sample outcouple photons from the resonant evanescent field, resulting in highly localized reductions of the reflected light intensity. By mapping changes in the resonant reflected peak intensity from the PC surface, components of a sample (e.g., focal adhesions) can be detected and dynamically tracked. To demonstrate the simplicity and utility of PROM for focal adhesion imaging, PROM images are compared with biosensor images of surface-bound dielectric permittivity and with fluorescence microscopy images of labeled adhesion molecules in dental stem cells. PROM can dynamically quantify the surface-attached cellular mass density and lateral dimensions of focal adhesion clusters.

20 Claims, 8 Drawing Sheets

(51) Int. Cl.
*G01N 21/25* (2006.01)
*G01N 21/27* (2006.01)
*G02B 21/00* (2006.01)
*G01N 21/552* (2014.01)

(52) U.S. Cl.
CPC ........... *G01N 21/552* (2013.01); *G02B 21/00* (2013.01); *G01N 21/6458* (2013.01)

(58) Field of Classification Search
CPC .......... G02B 21/00; G02B 21/32; G02B 6/12; G02B 1/00
See application file for complete search history.

(56) References Cited

U.S. PATENT DOCUMENTS

| | | | |
|---|---|---|---|
| 7,292,336 | B2 | 11/2007 | Cunningham et al. |
| 7,298,477 | B1 | 11/2007 | Cunningham et al. |
| 7,479,404 | B2 | 1/2009 | Cunningham et al. |
| 7,521,769 | B2 | 4/2009 | Cunningham et al. |
| 7,531,786 | B2 | 5/2009 | Cunningham et al. |
| 7,737,392 | B2 | 6/2010 | Cunningham et al. |
| 7,742,662 | B2 | 6/2010 | Cunningham |
| 7,968,836 | B2 | 6/2011 | Cunningham et al. |
| 8,298,780 | B2 | 10/2012 | Wagner et al. |
| 9,400,353 | B2 | 7/2016 | Cunningham et al. |
| 2016/0047944 | A1* | 2/2016 | Erickson ................ G02B 1/005 435/5 |

OTHER PUBLICATIONS

W. Chen, K. D. Long, M. Lu, V. Chaudhery, H. Yu, J. S. Choi, J. Polans, Y. Zhuo, B. A. Harley, and B. T. Cunningham, "Photonic crystal enhanced microscopy for imaging of live cell adhesion," Analyst, vol. 138, pp. 5886-5894, Aug. 22, 2013.

W. L. Chen, K. D. Long, H. J. Yu, Y. F. Tan, J. S. Choi, B. A. Harley, and B. T. Cunningham, "Enhanced live cell imaging via photonic crystal enhanced fluorescence microscopy," Analyst, vol. 139, pp. 5954-5963, Nov. 21, 2014.

Y. Zhuo, J. S. Choi, T. Marin, H. Yu, B. A. Harley, and B. T. Cunningham, "Quantitative Imaging of Cell Membrane-associated Effective Mass Density Using Photonic Crystal Enhanced Microscopy (PCEM)," Progress in Quantum Electronics, vol. 50, pp. 1-18, 2016.

Y. Zhuo et al., "Label-Free Biosensor Imaging on Photonic Crystal Surfaces," Sensors 15, 21613-21635 (Aug. 28, 2015).

Y. Zhuo et al., "Single nanoparticle detection using photonic crystal enhanced microscopy," Analyst 139, 1007 (Jan. 8, 2014).

* cited by examiner

PHOTONIC RESONATOR OUTCOUPLER MICROSCOPY (PROM)

CROSS-REFERENCE TO RELATED APPLICATIONS

This application claims priority under 35 U.S.C. § 119(e) to U.S. Provisional Application No. 62/574,877, filed Oct. 20, 2017, the content of which is incorporated herein by reference.

STATEMENT REGARDING FEDERALLY SPONSORED RESEARCH

This invention was made with government support under CBET 11-32301 awarded by the National Science Foundation and under R01 DK099528 and R21 EB018481 awarded by the National Institutes of Health. The United States Government has certain rights in this invention.

BACKGROUND

Photonic Crystal Enhanced Microscopy (PCEM) is a label-free biosensor-based form of microscopy that has been used for quantitative, dynamic imaging of cell-surface interactions. See W. Chen, K. D. Long, M. Lu, V. Chaudhery, H. Yu, J. S. Choi, J. Polans, Y. Zhuo, B. A. Harley, and B. T. Cunningham, "Photonic crystal enhanced microscopy for imaging of live cell adhesion," *Analyst*, vol. 138, pp. 5886-94, 2013 and Y. Zhuo, J. S. Choi, T. Marin, H. Yu, B. A. Harley, and B. T. Cunningham, "Quantitative Imaging of Cell Membrane-associated Effective Mass Density Using Photonic Crystal Enhanced Microscopy (PCEM)," *Progress in Quantum Electronics*, vol. 50, pp. 1-18, 2016. The PCEM technique uses a nanostructured photonic crystal optical resonator as a substrate for cell attachment. Engagement of cell membrane components with the surface of the photonic crystal (PC) results in highly localized shifts in the resonant reflected wavelength from the biosensor. It was found that by using a modified bright field microscope cell-surface attachment could be visualized with a 0.6 μm×0.6 μm pixel resolution. The PC nanostructure interacts with broadband external illumination from a light emitting diode (LED) to establish an electromagnetic standing wave (an evanescent field) that extends only about 200 nm into the cell media. This PCEM approach is only responsive to cell membrane components that reside within the evanescent field, with the greatest response obtained for dielectric material that displaces the media closest to the PCT surface. As reported, PCEM images were acquired in time steps of about 30 seconds, thereby enabling live cell attachment "movies" to be developed. Because PCEM is label-free, it does not require photobleachable or cytotoxic reporters, enabling cells to be studied over extended time periods (up to days or weeks) to observe, for example, apoptosis, chemotaxis, and differentiation.

This previously reported cell imaging by PCEM uses an imaging modality in which the Peak Wavelength Value (PWV) of the resonant reflected peak is measured over the imaging field of view to derive images of Peak Wavelength Shift (PWS) that occur when cells attach to the PC surface. It was found that sequences of PWS images or "movies" clearly show the evolution of cell attachment through engagement of the lipid bilayer membrane and internal cell-associated proteins within the ~200 nm deep evanescent field region of the PC.

Focal Adhesions (FAs), or cell-matrix adhesions, are large specialized protein assemblies (including mechanosensing, cytoskeletal, and signaling proteins) typically located at the interface between the cell membrane and the extracellular matrix (ECM). FAs are critical for supporting cell membrane structure and for regulating signal transmission between the actin cytoskeleton and the transmembrane receptor integrins during adhesion and migration. New tools are needed for studying the dynamic behavior of FA clusters and their interaction with the ECM, which are fundamental to processes that include metastasis, apoptosis, and chemotaxis. The response of FA clusters to drugs is one approach by which the action of pharmaceutical compounds may be evaluated, where approaches that enable characterization to be performed with a small number of cells is especially valuable. During the dynamic assembly/disassembly of a FA, the size of the FA cluster varies, and is highly correlated with the level of adhesion engagement and migration speed. For example, non-mature Focal Complexes (FXs) are initially formed at the leading edge of the cell (e.g. in the lamellipodia area) and are smaller than 0.2 $\mu m^2$. As the lamellipodia withdraws from the leading edge, many FXs disassemble and release adhesion proteins back to the inner cell body, while some of the FXs grow larger (typically 1-10 $\mu m^2$) and assemble into mature FA clusters by recruiting adapter proteins. Once the remaining FAs are in place, they may form stationary attachment points by binding to the ECM. A cell may utilize such anchors to migrate over the ECM through pushing/pulling the whole cellular body.

The detailed mechanism of FA assembly/disassembly in live cells, including FA dimension variation, is poorly understood, although a variety of approaches have been utilized to investigate their mechanisms. Determining the dynamic dimension of a FA cluster (with all of the FA proteins simultaneously) is challenging, especially during the assembly/disassembly process in live cells. Fluorescent tags are typically used to mark individual focal adhesion proteins, but due to the temporal limitations imposed by photobleaching, accurate quantitation and long-term analysis are exceedingly difficult to perform. In addition, cytotoxicity of fluorescent tags can compromise the viability of the cells under study.

Accordingly, there is a need to provide label-free modalities that can be used to dynamically track focal adhesions and other cellular structures, processes, and interactions.

SUMMARY

In one aspect, example embodiments provide an instrument for photonic resonator outcoupler microscopy (PROM) of a sample on a surface of a photonic crystal. The instrument comprises a light source configured to emit incident light, an optical system, a spectrometer, a camera optically coupled to the spectrometer, and an analysis system. The optical system is configured to focus the incident light emitted by the light source to provide focused light that sequentially illuminates each linear region of a plurality of linear regions of the surface of the photonic crystal. The spectrometer is configured to (i) receive reflected light that has reflected from each linear region of the surface of the photonic crystal in response to illumination by the focused light and (ii) for each linear region, spectrally disperse the reflected light from the linear region into a set of spectra, wherein each spectrum in the set of spectra corresponds to a respective location in the linear region. The camera is configured to acquire a plurality of images, wherein each image corresponds to a particular linear region of the plurality of linear regions and records the set of spectra of the particular linear region. The analysis system is configured to (i) analyze the acquired images to identify for each location in each linear region of the surface of the photonic crystal, a respective resonant wavelength in the spectrum for the location and a respective intensity value of the respective resonant wavelength, so as to obtain a plurality of intensity values, and (ii) generate a PROM image of the sample based on the plurality of intensity values, wherein different intensity values in the PROM image are indicative of different amounts of resonant wavelength scattering by components of the sample at different locations.

In another aspect, example embodiments provide a method for photonic resonator outcoupler microscopy (PROM) of a sample on a surface of a photonic crystal. The method involves emitting incident light from a light source, focusing the incident light by an optical system to provide focused light, and sequentially illuminating with the focused light each linear region of a plurality of linear regions of the surface of the photonic crystal. The method further involves a spectrometer receiving reflected light that has reflected from each linear region of the surface of the photonic crystal in response to illumination by the focused light and, for each linear region, the spectrometer spectrally dispersing the reflected light from the linear region into a set of spectra, wherein each spectrum in the set of spectra corresponds to a respective location in the linear region. The method also involves a camera optically coupled to the spectrometer acquiring a plurality of images, wherein each image corresponds to a particular linear region of the plurality of linear regions and records the set of spectra of the particular linear region. The method additionally involves analyzing the acquired images to identify for each location in each linear region of the surface of the photonic crystal a respective resonant wavelength in the spectrum for the location and a respective intensity value of the respective resonant wavelength, so as to obtain a plurality of resonant wavelengths and a plurality of intensity values, and generating a PROM image of the sample based on the plurality of intensity values, wherein different intensity values in the PROM image are indicative of different amounts of resonant wavelength scattering by components of the sample at different locations.

BRIEF DESCRIPTION OF THE DRAWINGS

FIG. 7a is a bar graph comparing the fluorescent intensities from the edge and inner portions of the cell in the actin, nucleus, and vinculin images shown in FIG. 6a.

FIG. 7b is a bar graph comparing the PIS data from the edge and inner portions of the cell in the PIS image shown in FIG. 6a.

FIG. 7c is a bar graph comparing the PWS data from the edge and inner portions of the cell in the PWS image shown in FIG. 6a.

DETAILED DESCRIPTION

1. Overview

Figure 1:
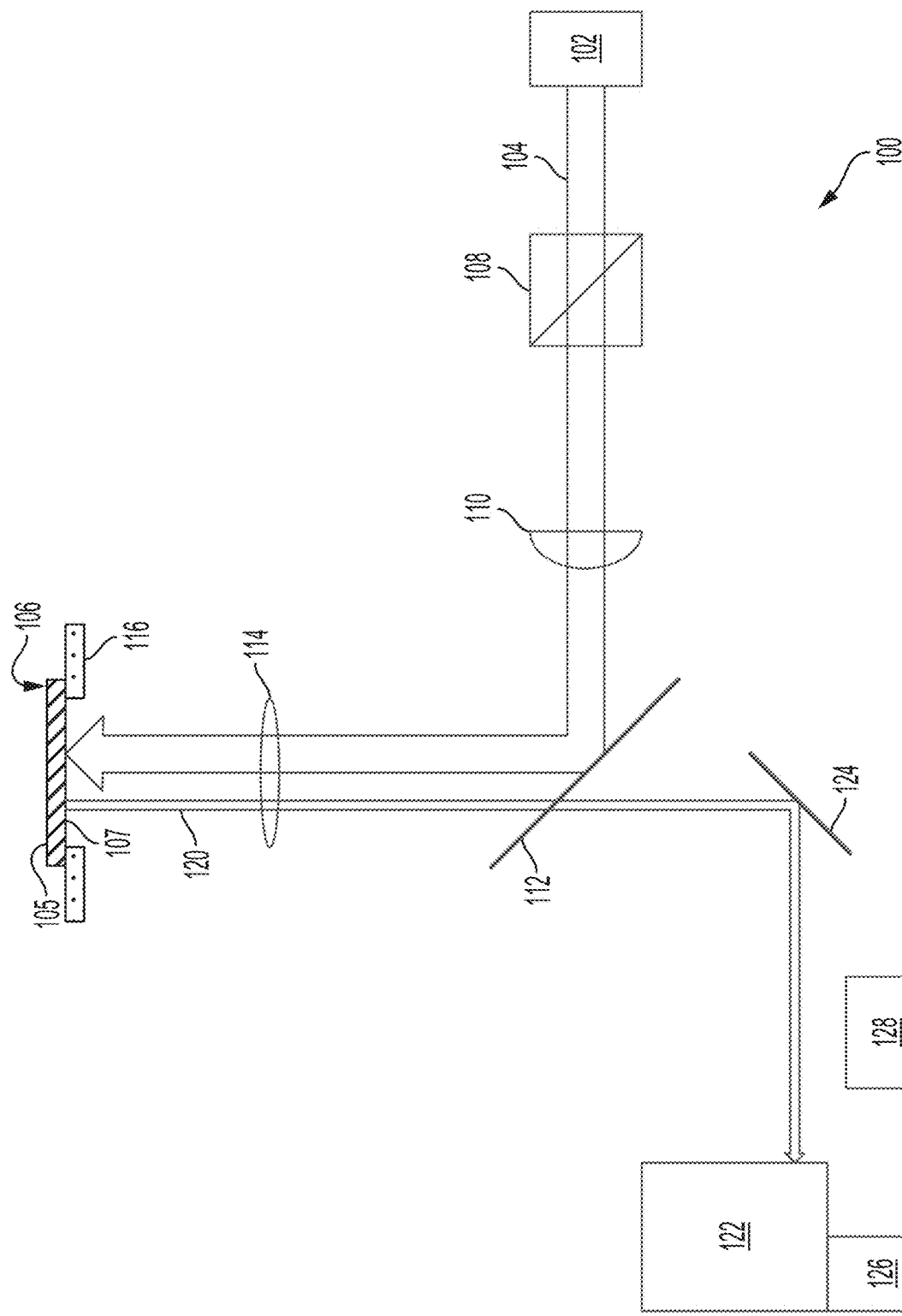
FIG. 1 is a schematic diagram of a PROM instrument, in accordance with an example embodiment.

In previously reported PCEM approaches, the effects of a dielectric material on a PC surface were sensed by its dielectric permittivity, which causes a shift in the resonant Peak Wavelength Value (PWV). Thus, PCEM images represented spatial maps of PWV shifts corresponding to locations of increased cell attachment density or the locations of dielectric particles such as polymers, viruses, or cells. Disclosed herein is an orthogonal and complementary form of microscopy in which changes in the resonant reflection efficiency from a PC surface are measured on a pixel-by-pixel basis to form an image. Two mechanisms exist for locally reducing the reflected intensity from a PC at the resonant wavelength: absorption and scattering.

The absorption mechanism is believed to work in the following manner. A substance that possesses optical absorption at the resonant wavelength of the PC will locally reduce the intensity of the resonant wavelength due to a mechanism through which the attached material (i.e. within the evanescent field region on the surface of the PC) gathers energy into itself, where it is dissipated by heating the surrounding environment. If the reflected intensity from the PC is observed at the PC resonant wavelength, one would observe a "hole" in the reflected intensity, at the location of the optical absorber.

The scattering mechanism is believed to work in the following manner. A material attached to the PC surface that is not an optical absorber may also cause a localized reduction in the intensity of the resonant wavelength if the material has sufficient dielectric permittivity contrast to its surrounding environment to outcouple light from the PC by scattering. This mechanism in which a reduction in the intensity of the reflected resonant wavelength from the PC is observed due to outcoupling of resonant standing wave photons enables a new form of microscopy described herein as Photonic Resonator Outcoupler Miscroscopy (PROM).

In example implementations, PROM is used to observe the dynamics of live cell attachment to a PC surface. The resonant reflected Peak Intensity Value (PIV) from the PC is measured before and after live cell attachment to acquire the Peak Intensity Shift (PIS) at each local pixel area. Images of the PIS reveal highly localized and easily observed loci of protein clusters that correlate with the spatial distribution and size of focal adhesions observed by fluorescence microscopy. Focal adhesions (FAs) are the mechanism through which cells attach to surfaces through processes that include stem cell differentiation, chemotaxis, metastasis, tumor proliferation, and apoptosis, and thus drugs often target biological pathways that modulate focal adhesion formation. The formation of FAs is associated with localized accumulation of proteins that span from outside the cell membrane to within the cell membrane. This process generates a sufficiently localized region of high refractive index compared to the surrounding cell material that localized scattering occurs, which couples light out of the PC at the resonant wavelength. In this way, PROM is capable of measuring the dynamic formation of FAs at the interface between cells and the surfaces to which they attach. More generally, PROM is a new tool for observing biological processes (e.g., cell attachment) and for evaluating the effects of environmental changes (e.g., the influence of drugs) on such processes.

To demonstrate the utility of PROM for focal adhesion imaging, dental stem cells attaching to a fibronectin-coated PC surface were studied as a representative example. It was found that PWS and PIS images of the same cells display distinct and complementary information. While regions of greatest PWS represent the locations at the cell-surface interface in which uniformly distributed regions with the greatest surface engagement occur, regions with the greatest PIS represent the formation of highly concentrated protein clusters at the cell-surface interface (e.g., FAs) that are capable of scattering photons.

2. Example Photonic Crystals (PCs)

The PCs described herein are subwavelength nanostructured surfaces with a periodic modulation of refractive index that acts as a narrow bandwidth resonant optical reflector at one specific wavelength. The high reflection efficiency of the PC at the resonant wavelength is the result of the formation of surface-confined electromagnetic standing waves that extend into the surrounding medium in the form of an evanescent electromagnetic field. The photonic band gap of the PC strictly limits lateral propagation of light, and thus the PC exhibits strong optical confinement of incident light into a small volume that interacts selectively with surface-adsorbed cell components, while being insensitive to the components of the cell body that are not engaged with the surface. Various aspects of Photonic crystal biosensors are described in U.S. Pat. Nos. 7,479,404, 7,521,769, 7,531,786, 7,737,392, 7,742,662, and 7,968,836, which patents are incorporated herein by reference.

Previous research has demonstrated that a specific location on the PC surface has a resonant reflected wavelength that can be independently measured from neighboring regions, and that the local PWV is determined by the dielectric permittivity of biomaterial that is adsorbed at that specific location. See Y. Zhuo, H. Hu, W. L. Chen, M. Lu, L. M. Tian, H. J. Yu, K. D. Long, E. Chow, W. P. King, S. Singamaneni, and B. T. Cunningham, "Single nanoparticle detection using photonic crystal enhanced microscopy," *Analyst*, vol. 139, pp. 1007-1015, 2014. The PC surface can therefore act as a proxy for a biological surface with a built-in capacity to detect changes in the cell membrane components of cells that attach to the PC within the evanescent-field, thus providing a compelling platform for adhesion phenotyping of single cells. PC biosensor surfaces can be inexpensively fabricated uniformly over large surface areas by a room temperature nanoreplica molding process and can be incorporated onto glass microscope slides.

For the dental stem cell studies reported herein, the PC is comprised of a 1-dimensional UV-curable polymer grating surface structure ($n_{UVCP}$=1.5, grating depth d=120 nm, period Λ=400 nm, duty cycle f=50%) coated with a thin film of $TiO_2$ ($n_{TiO2}$=2.4, thickness t=80 nm). With these parameters, the PC has a resonant wavelength near 625 nm. A room temperature replica molding approach is used to fabricate the PC on a plastic substrate, using a quartz master template with a negative volume image of the desired grating structure fabricated with e-beam lithography and reactive ion etching. Liquid UV curable polymer is deposited between the wafer template and glass substrate, and exposure with a high intensity UV lamp is used to cure the polymer to a solid state. After peeling the grating replica away from the quartz mold template, the nano-patterned surface is attached to a glass cover slip with adhesive. PC fabrication is completed by reactive sputter deposition of $TiO_2$ atop the grating structure. To prepare for cell attachment experiments, the PC is cleaned by sonication in isopropyl alcohol and water for one minute each, followed by drying with nitrogen gas. The PC is also treated with oxygen plasma to facilitate attachment of a liquid containment gasket formed from polydimethylsiloxane (PDMS). Finally, the PC surface is hydrated with phosphate buffered saline solution and coated with a layer of fibronectin to promote cellular attachment.

3. Example PROM Instrument

The PROM instrument is a modified brightfield microscope that uses a line-scanning approach to measure the spatial distribution of PWV and PIV across a PC surface with submicron spatial resolution for label-free imaging. A schematic diagram of an example PROM instrument 100 is shown in FIG. 1. In this example, the PROM instrument 100 includes an LED 102 as a light source. The specific LED used for the experiments reported herein was a Thorlabs M617F1 fiber-coupled LED, with a nominal wavelength of 617 nm and a bandwidth (FWHM) of 18 nm. Light 104 emitted from the LED 102 is directed to a PC 106 via a polarizing beam splitter (PBS) cube 108, cylindrical lens 110, beamsplitter 112, and objective lens 114. The PBS cube 108 linearly polarizes light 104 so that the electric field vector is oriented perpendicular to the grating structure when incident upon the PC. The cylindrical lens 110 focuses the light 102 to a line at the back focal plane of the objective lens 114 via the beamsplitter 112. In representative examples, the cylindrical lens 110 has a focal length of 200 mm and the objective lens 114 is a 10× or 40× microscope objective.

The PC 106 has an upper surface 105 where the sample (not shown) is placed and a lower surface 107 opposite the upper surface 105. The PC 106 is illuminated from below at normal incidence (e.g., illuminated through the lower surface 107) by the light 104 passing through objective lens 114. The objective lens 114 focuses the light 102 to a focal line on the surface of the PC 106 such that the focal line is substantially perpendicular to the grating direction. Illumination from below can beneficially reduce or eliminate scattering or absorption from cell materials attached to PC 106. To illuminate different portions of the PC 106, the lower surface 107 of PC 106 is supported on a motorized stage 116. The motorized stage 116 can move the PC 106 relative to the objective lens 114 so that different linear regions of the upper surface 105 can be illuminated by the focused light from the objective lens 114.

The reflected light 120 from the PC 106 contains the resonant reflected spectrum. The reflected light 120 passes through the objective lens 114 (in a direction opposite to that of light 104) and is directed to an entrance slit (30 µm wide) at the input of an imaging spectrometer 122 via beamsplitter 112 and mirror 124. The imaging spectrometer 122 is coupled to a CCD camera 126, which records the spectrum of the reflected light 120 as an image. Each image recorded by the CCD camera 126 includes the spectrum for each pixel across a line on the PC 106 that is illuminated by light 104. In the system used for the dental stem cell studies reported herein, the spectrometer 122 was a grating-based spectrometer (300 lines/mm from Acton Research Corp.) and the CCD camera 126 had 512×512 pixels (Photometrics Cascade 512).

Using this method, reflected light is collected from a linear region of the PC 106, where the width of the imaged line (e.g., 1.2 µm) is determined by the width of the entrance slit of the imaging spectrometer and the magnification power of the objective lens. The line of reflected light, containing the resonant biosensor signal, is diffracted by the grating within the spectrometer to produce a spatially resolved spectrum for each point along the line. Each pixel across the line is converted to a resonant reflection spectrum containing a narrow bandwidth ($\Delta\lambda$~4 nm) reflectance peak from the PC. The Peak Wavelength Value (PWV) and Peak Intensity Value (PIV) of each peak are determined by fitting the spectrum to a $2^{nd}$ order polynomial function, and then mathematically determining the maximum wavelength of the function. By fitting all 512 spectra, a line of 512 pixels is generated that represents one line of a PWV or PIV image of the sample on PC surface. With a 10× objective lens and an effective magnification of 26×, each pixel in the line represents a ~0.6 µm width on the PC surface and 512 such pixels cover a total width of ~300 µm (x dimension).

The PIV may be determined by multiple possible methods. For example, the intensity value assigned to a peak may be determined by simply reading the magnitude of the highest intensity wavelength in the reflected spectrum. Alternatively, the intensity of the reflected peak may be determined by integrating the reflected intensities over a range of wavelengths that comprise part or all of the reflected wavelengths. Further, the PIV value may be normalized by dividing the measured intensity of a peak by a reflected intensity of known value, such as the intensity reflected by a mirror, or by the intensity of a "clean" portion of the PC that is known to be free of surface-adsorbed biological material.

To generate a two-dimensional PIV image (PROM image) of the sample on the PC surface, the motorized stage 116 (Applied Scientific Instruments, MS2000) translates the PC 106 along the axis perpendicular to the imaged line (y dimension) in increments of 0.6 µm/step. Using this technique, a series of lines are assembled into an image at a rate of 0.1 sec/line and the same area on the PC surface can be scanned repeatedly. Each image is comprised of 512 by n pixels, where n can be selected during each scan session, and each pixel represents a 0.6×0.6 µm² region of the PC surface. The PROM instrument and sensor structure measures the resonant reflection characteristics of the PC via the spectrum obtained from each 0.6×0.6 µm² pixel, representing about a 300×300 µm² region of the PC surface. High spatial resolution in the axial direction is obtained due to the shallow evanescent-field of the PC. Resolution in the lateral direction is determined by the lateral propagation distance of resonant-coupled photons, resulting in detection of distinct surface-attached objects for widely dispersed features at the 10-100 nm size scale.

The PROM image can be generated by an analysis system 128 coupled to the CCD camera 126. The analysis system 128 may also control the motorized stage 116. The analysis system 128 could be, for example, a computing device that is programmed with software for analyzing the images acquired by the CCD camera 126 to determine resonant wavelengths and intensities of resonant wavelengths and to generate PROM images (the analysis system 128 could also generate PWS images based on PWV shifts). Thus, in one example, the analysis system 128 includes a processor and non-transitory data storage that stores instructions that are executable by the processor to perform any of the functions described herein.

It has been found that small non uniformities may appear in the PWV or PIV "background" of as-fabricated PCs due to slight variation of $TiO_2$ thickness or nonuniformity of the extracellular matrix (ECM) coating used to promote cell adhesion. To eliminate the nonuniform background, the initial PWV or PIV of a blank PC immersed in cell media (before cell attachment) can be subtracted from the PWV or PIV after cell attachment on a pixel-by-pixel basis to generate the peak wavelength shift (PWS) or peak intensity shift (PIS) images.

Figure 2:
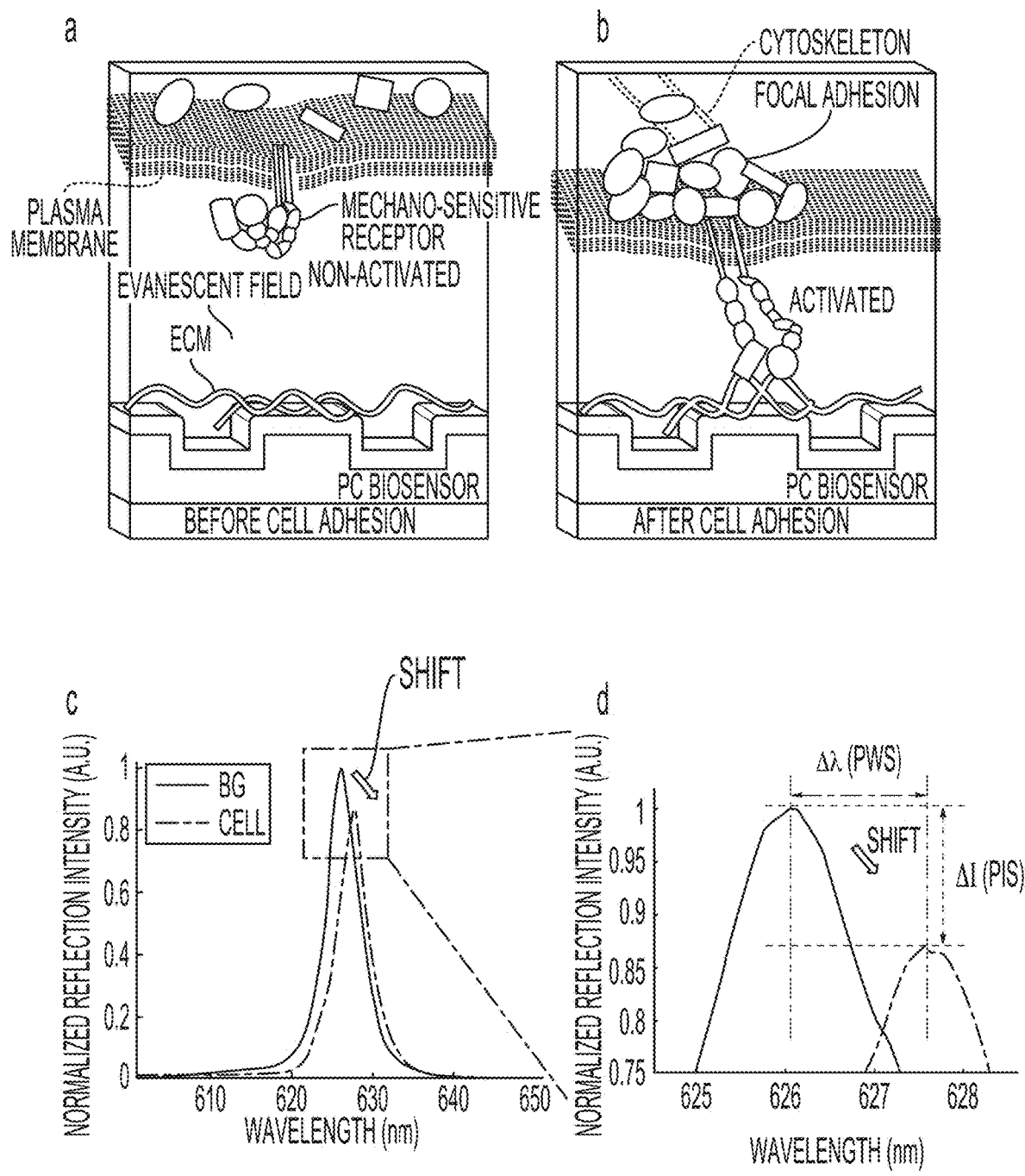
FIG. 2 includes schematic representations of cellular structures (a) before and (b) after cell adhesion to a PC biosensor surface, (c) a resonant reflection spectra before and after the cell attaches to the PC surface, and (d) a magnified view of the tips of the resonant peaks, in accordance with an example embodiment.

When a cell attaches to the PC surface, the peak resonant wavelength red-shifts from a shorter wavelength to a longer wavelength. FIG. 2 includes schematic representations of cellular structures (a) before and (b) after cell adhesion to the PC biosensor surface. FIG. 2 also shows (c) example resonant reflection spectra before and after the cell attaches to the PC surface. In this example, the shift is from $\lambda_{BG}$≈626 nm before cell attachment to $\lambda_{cell}$≈628 nm after cell attachment. This increase in wavelength (positive PWV shift) indicates that a first material in contact with the PC surface is replaced by a second material that has a higher refractive index. For example, water with a refractive index of $n_{water}$=1.33 may be replaced by cellular materials with a refractive index of $n_{cell}$=1.35-1.38. As higher densities of cell membrane components and intracellular protein components of cell membranes associated with focal adhesions appear on the PC surface, the magnitude of the local refractive index will increase. Therefore, the PWS image represents the mass density distribution of cell components. At the same time, the resonant reflection efficiency, as measured by the peak intensity, changes from a higher PIV before cell attachment to a lower PIV after cell attachment. FIG. 2 shows (d) a magnified view of the tips of the resonant peaks shown in (c). In this example, with the peak wavelength intensity before cell attachment normalized to 1, the peak wavelength intensity after cell attachment decreases to 0.85. The negative PIV shift (PIS) indicates that the proteins in some areas of the cell are binding with transmemberane proteins (e.g., integrins) to form more substantial focal adhesion clusters. This, in turn, increases scattering of the resonant wavelength, which lowers the PIV.

4. Computer Modeling of Resonant Outcoupling from a PC by a Focal Adhesion

Using the PROM instrument described herein, it is possible to obtain both PIV images and PWS images of cell attachment to a PC surface. Interestingly, characteristics of the PIV images of cell attachment obtained in this way can differ substantially from the PWS images. The physical mechanism responsible for PIV reduction in the context of cell attachment can explain why the PIV images can be substantially different than the PWS images.

Theoretical and experimental analysis suggests that reduction in the PIV can occur by two mechanisms. First, materials that act as absorbers of the resonant wavelength efficiently and locally quench the PC resonance. Second, concentrated local regions of high dielectric permittivity can outcouple resonantly confined light via scattering. Of these two mechanisms, outcoupling via scattering (PROM) is expected to be the dominant mechanism for PIV reduction in the case of cell adhesion to a PC surface. Although optical absorption at the PC resonant wavelength ($\lambda$=625-635 nm) will efficiently reduce the PIV in a highly localized manner, the protein and lipid components of cells and cell membranes do not display strong absorption in the visible wavelength range ($\lambda$=400~700 nm). Human tissues and live cells exhibit strong absorption in the infrared, but these wavelengths are not utilized in the PROM instrument described herein, and thus do not contribution to PIV reduction. While metallic elements comprise a small fraction of a cell's atomic constituency, metal atoms are present as ions rather than as clusters capable of optical absorption in the visible part of the spectrum. On the other hand, scattering occurs when light is forced to deviate from its original trajectory due to localized non-uniformities in its propagation medium, which occurs, for example, when light propagating through water is reflected or refracted by a particle with a greater refractive index. A highly concentrated region (e.g., focal adhesion cluster) of greater refractive index than its surroundings (e.g., cell media) generates more localized and efficient scattering than a diffuse region with gradual gradient in the refractive index transition. Scattering effects also become stronger when the size of a region with refractive index contrast increases. Since the cross sectional area of an FA cluster is typically 0.2-1.0 $\mu m^2$, it is expected to observe measurable differences in the scattering efficiency of membrane-associated protein clusters as they form, change size, and subsequently dissipate. Thus, PROM can be used to detect changes in membrane-associated scattering that occur due to FA formation and dissipation by taking advantage of the ability of localized high refractive index protein clusters to produce image contrast through reduction of the reflection efficiency of a PC biosensor.

Figure 3:
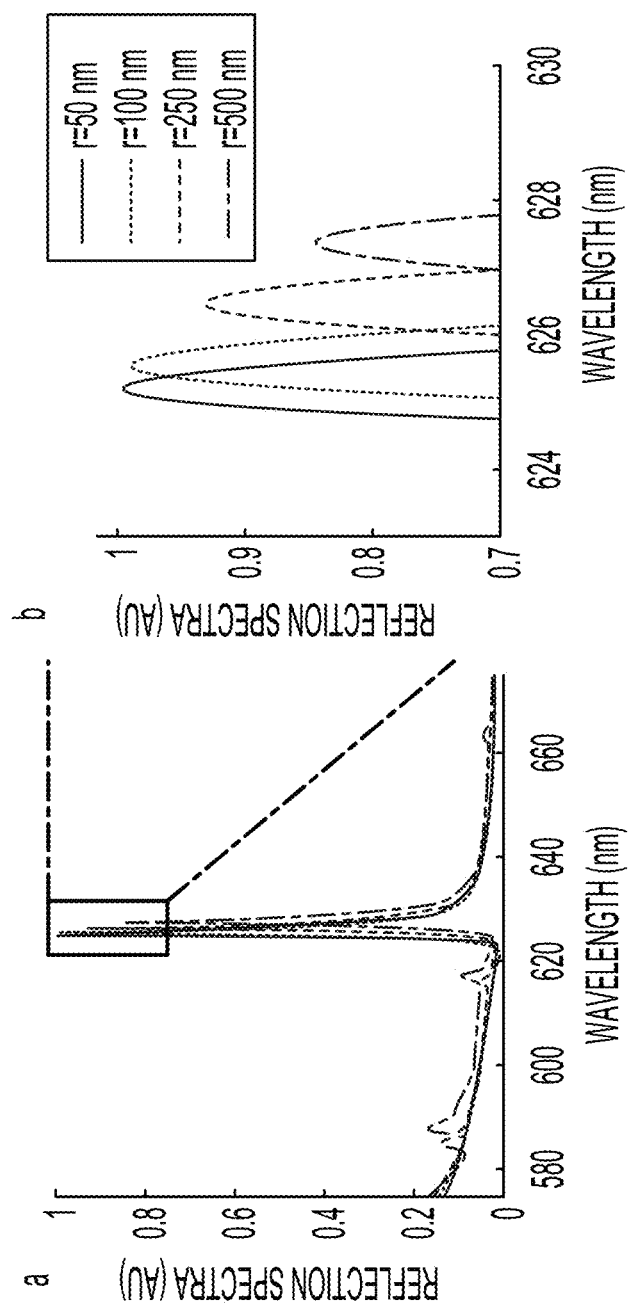
FIG. 3 shows the results of Finite Difference Time Domain (FDTD) computer simulations that may relate to example embodiments.

A 3D Finite Difference Time Domain (FDTD) computer model supports the hypothesis that the dominant cause for the PIV reduction associated with a FA adhering to a PC surface is light scattering rather than absorption. Scattering describes the effect of an electromagnetic plane wave propagating through a dielectric particle. The FDTD computer model (using software from Lumerical Solutions, Inc.) was used to simulate an FA on a PC surface. The FA was represented as a homogeneous, lossless sphere with a designated radius from 50 to 500 nm and a designated refractive index greater than the surrounding medium. Specifically, a refractive index of n=1.46 was used to model the FA material, so as to approximate the refractive index of a sphere made up of about 75% protein and 25% water. A refractive index of n=1.333 was used to model the surrounding medium. In the FDTD computer model, these refractive indices were held constant while the radius of the FA material was modeled at 50, 100, 250, and 500 nm. The PC was modeled with a grating period of 400 nm and duty cycle of 50% and coated with 81 nm of $TiO_2$. The simulation used three PC periods with one nanoparticle in the center. The incident light in the model was a p-polarized plane wave that illuminated the PC from beneath. Periodic boundary conditions were applied in the direction perpendicular to the PC grating structure, and perfectly matched layer (PML) boundary conditions were used in the other directions. The mesh cube was $10^3$ $nm^3$ throughout the simulation space. The results of the FDTD simulation are shown in FIG. 3.

These results demonstrate that as the radius of the FA material increases, the peak wavelength shifts to higher wavelength and the peak intensity decreases, as expected for scattering-induced outcoupling. For comparison, a FDTD simulation was also run in which only the bulk refractive index of the liquid media in contact with the PC is increased. In that comparative simulation, the increase in the refractive index caused the peak reflected wavelength to shift to higher values but did not modify the reflected intensity.

5. Dynamic PIS Images of Live Cells

Figure 4A:
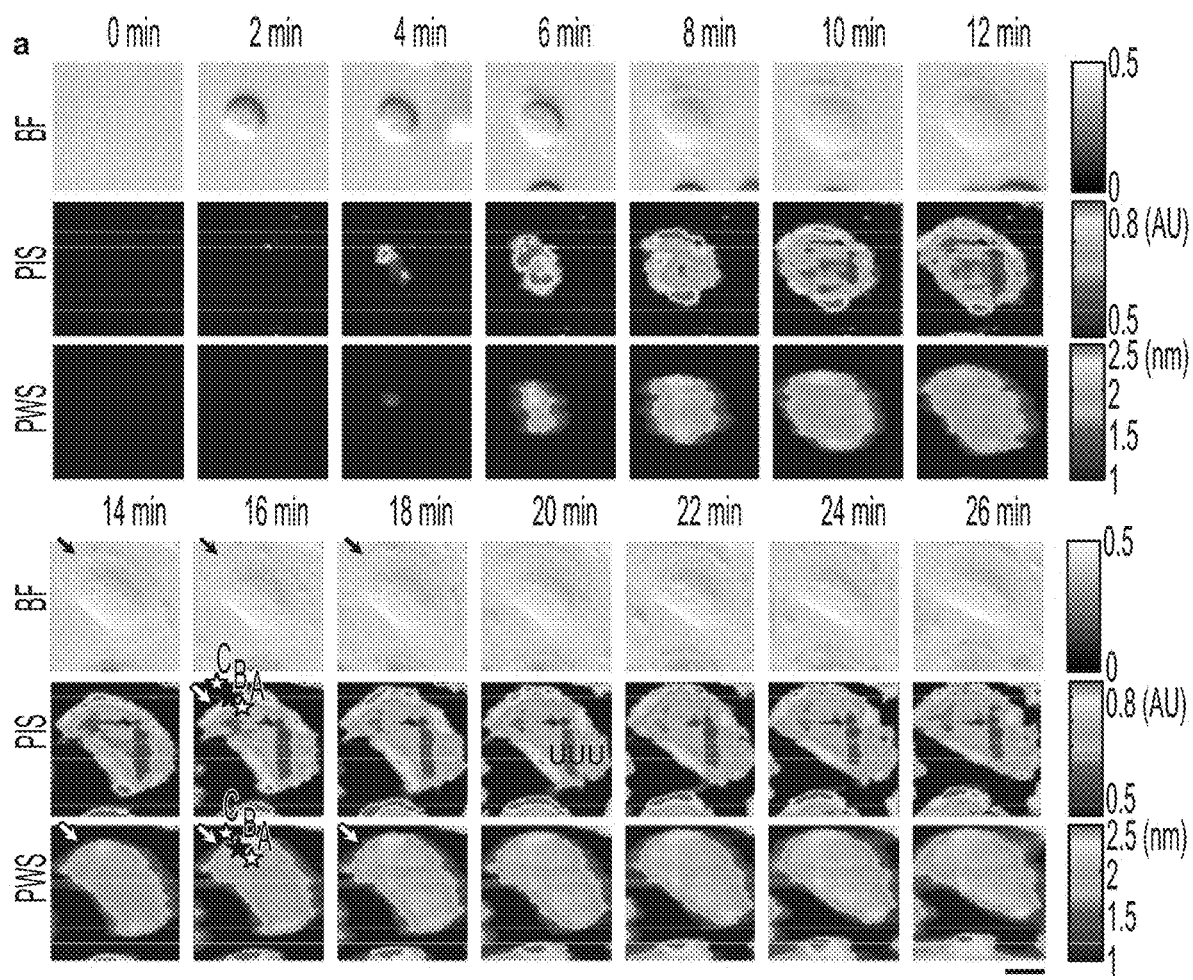
FIG. 4a shows brightfield (BF), peak intensity value (PIV), and peak wavelength shift (PWS) images of a live cell adhering to a PC surface over a period of time, in accordance with an example embodiment.
Figure 4B:
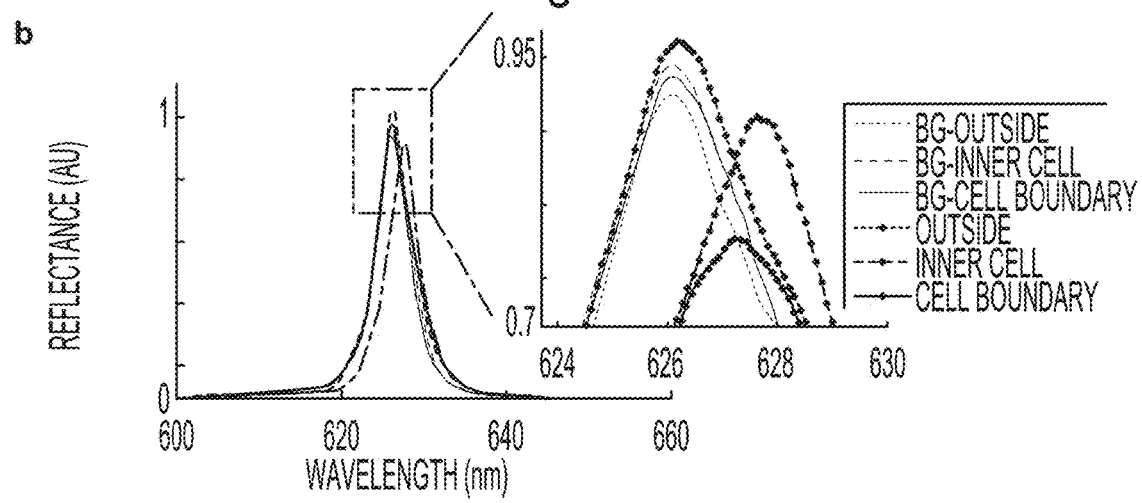
FIG. 4b shows reflectance spectra for three different locations shown in FIG. 4a before and after cell adhesion, in accordance with an example embodiment.

FIGS. 4a and 4b show the results of imaging live cells using the PROM instrument described herein. The live cells were murine dental epithelial stem cells (mHAT9a). The cells were maintained in Dulbecco's Modified Eagle Medium (DMEM) supplemented with 10% fetal bovine serum (FBS) and 1% Penicillin Streptomycin (PenStrep).

FIG. 4a shows a sequence of PROM-acquired images at several points in time during the cell adhesion process (0 minutes through 26 minutes, in 2-minute increments). Three images are shown for each point in time: a brightfield (BF) image; a peak intensity shift (PIS) image; and a peak wavelength shift (PWS) image. In the PIS images, greater reductions in reflection efficiency are displayed as higher intensity values for simpler visual comparison with other imaging modalities. As shown in FIG. 4a, the PIS image sequence reveals that the cell periphery generally demonstrates a greater degree of scattering than the cell center. This ring effect demonstrates that the PIS intensity is not homogeneously distributed throughout the cell membrane.

FIG. 4b shows PROM spectra from three sample points marked in FIG. 4a (A, B, and C) measured at two points in time: before cell adhesion (dashed lines) and after cell adhesion (solid lined). Initially, all three points are located outside of the cell, and all points show high resonant peak value as highlighted by the dashed line in the spectra (FIG. 4b). During cell adhesion, the boundaries are expanded and passed by the three points as the cell extends its attachment area. Near the end of the adhesion process, (i.e., 16 min), point A represents a location inside of the boundary, point B represents a location near the cell boundary, and point C represents a location outside of the cell boundary. The solid lines in FIG. 4b demonstrate that the spectrum of point A shifts to a relatively lower resonance peak value, point B shifts to the lowest resonance peak value, and point C remains at the original resonance peak value. Considering all the pixels within the cell, these results show a ring of enhanced scattering that encompasses much of the cell periphery.

FIGS. 4a and 4b also allow a comparison between the PWS images and the PIS images for the same cell at each point in time. In FIG. 4b, the dashed lines represent the background spectra for pixel locations A, B, and C acquired before cell attachment (0 minutes), and the solid lines (with dot markers) represent the spectra of the same pixel locations A, B, and C after cell attachment (16 minutes). The PWS and PIS images are extracted from the peak wavelength value and peak intensity value simultaneously (from the spectra at each ~0.6×0.6 $\mu m^2$ pixel area on the PC surface). FIG. 4a demonstrates that regions of greatest values in PWS and PIS images show distinct distribution patterns, which suggests that they likely represent two different physical mechanisms. For instance, the PWS image of the cell marked by the white arrow shows high peak wavelength shift on the top and bottom of the cell body, while the PIS image of the same cell shows a "ring" of high peak intensity shift along the cell boundary.

Figure 5A:
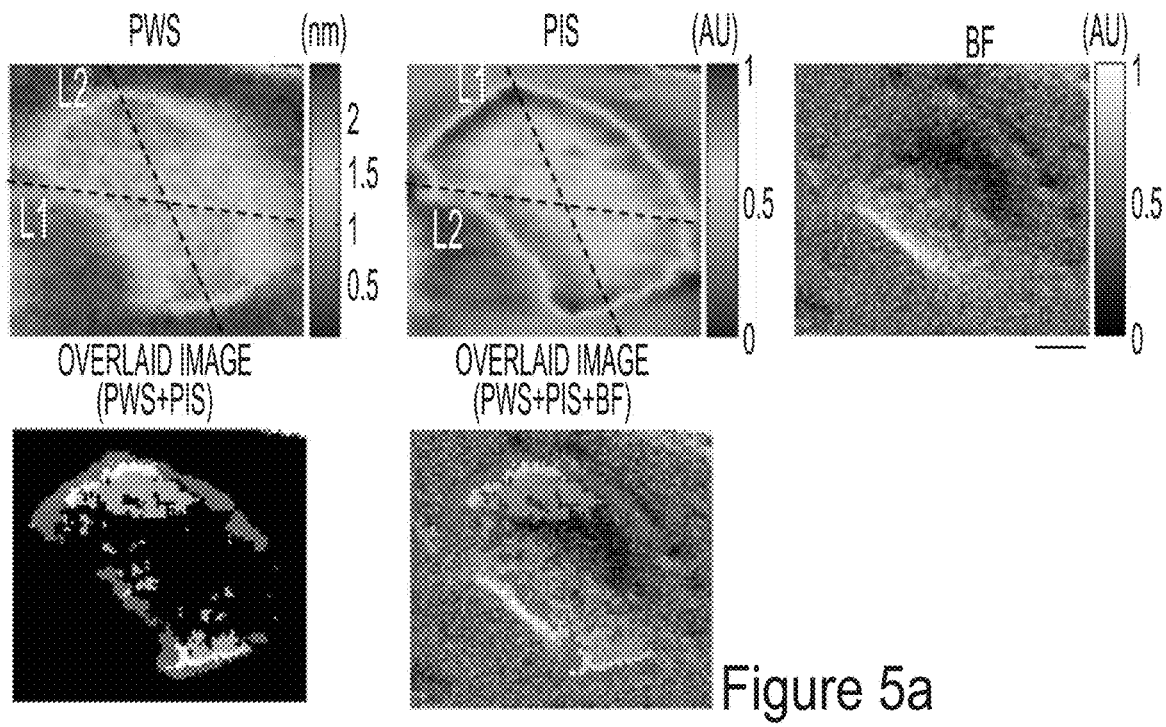
FIG. 5a shows PWS, PIS, BF, and overlaid images of a cell on a PC surface, in accordance with an example embodiment.
Figure 5B:
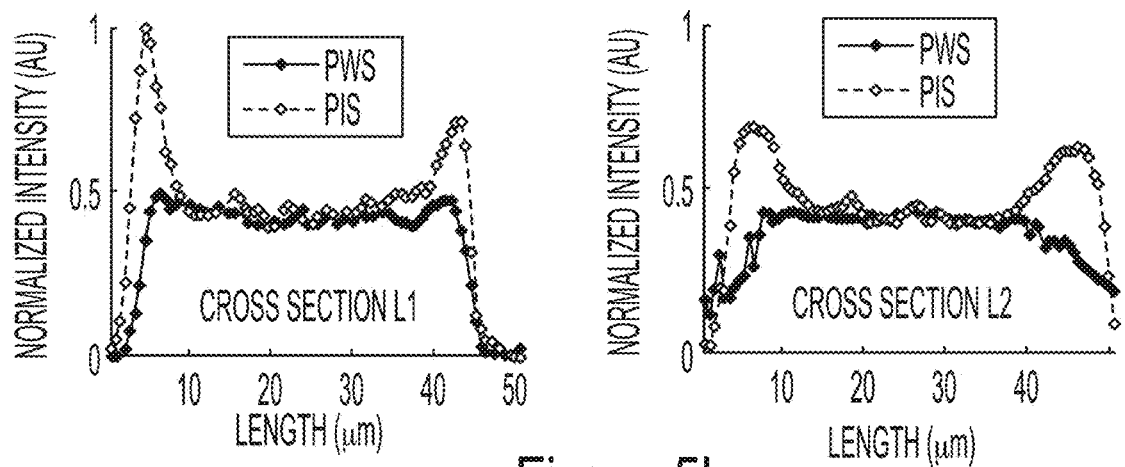
FIG. 5b shows the PWS data and PIS data taken along cross section lines L1 and L2 through the cell shown in FIG. 5a, in accordance with an example embodiment.
Figure 5C:
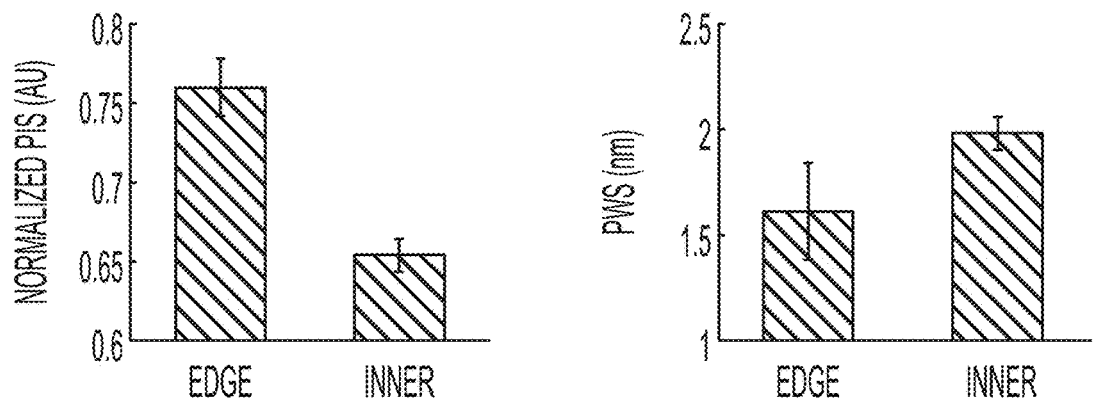
FIG. 5c shows bar graphs comparing the PIS data and the PWS data from the edge of the cell and the inner portion of the cell shown in FIG. 5a, in accordance with an example embodiment.

FIG. 5a shows images (PWS, PIS, BF, and overlaid images) of a single cell about 12 minutes after the cell was introduced. The PWS and PIS images show distinct distribution patterns. FIG. 5b shows the PWS and PIS data taken along cross section lines L1 and L2 through the cell (the LI and L2 lines are shown in FIG. 5a). FIG. 5c shows (on the left) a bar graph comparing the PIS data at the edge of the cell with the PIS data in the inner portion of the cell and (on the right) a bar graph comparing the PWS data at the edge of the cell with the PWS data in the inner portion of the cell. The bar graphs in FIG. 5c indicate that the PIS data and the PWS data have different distributions between the edge and inner portions of the cell.

The higher intensity of PWS (on the top and bottom of FIG. 5a) represents higher mass density of cellular materials associated with the cell membrane, whereas the higher intensity of PIS along the cell boundary represents the scatter outcoupling effect from the locally generated FA clusters. Typically, greater cluster size of the protein aggregates correspond to greater PIV reduction compared with the background. These measurements of local PWS and PIS can quantify the surface-attached cellular mass density and dimension of the FA clusters dynamically and simultaneously.

6. Comparison of PIS Images and Fluorescent Images

Figure 6A:
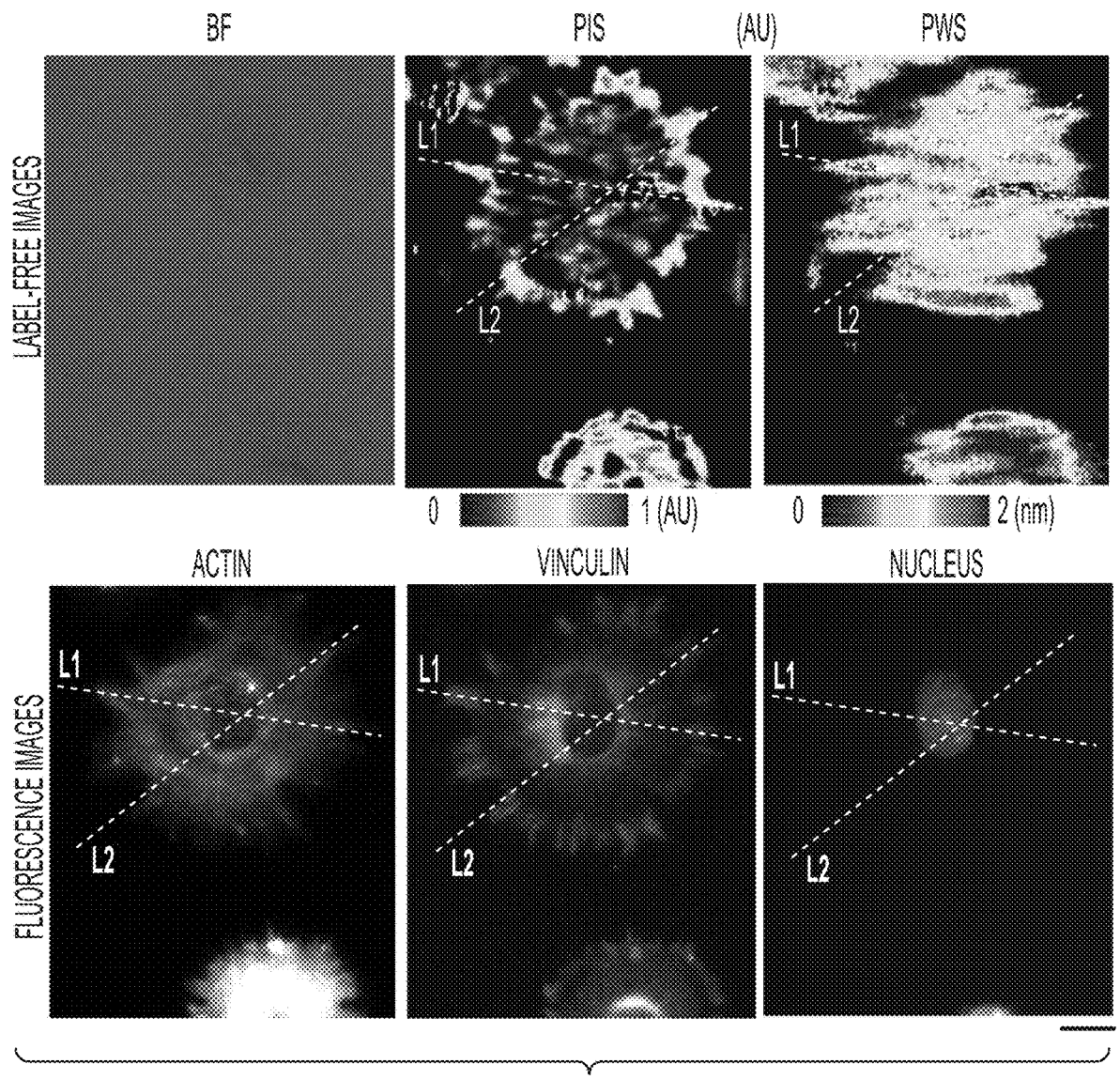
FIG. 6a shows BF, PIS, and PWS images of a cell and fluorescent images of the cell with fluorescent tags applied to actin, vinculin, and the nucleus, in accordance with an example embodiment.
Figure 6B:
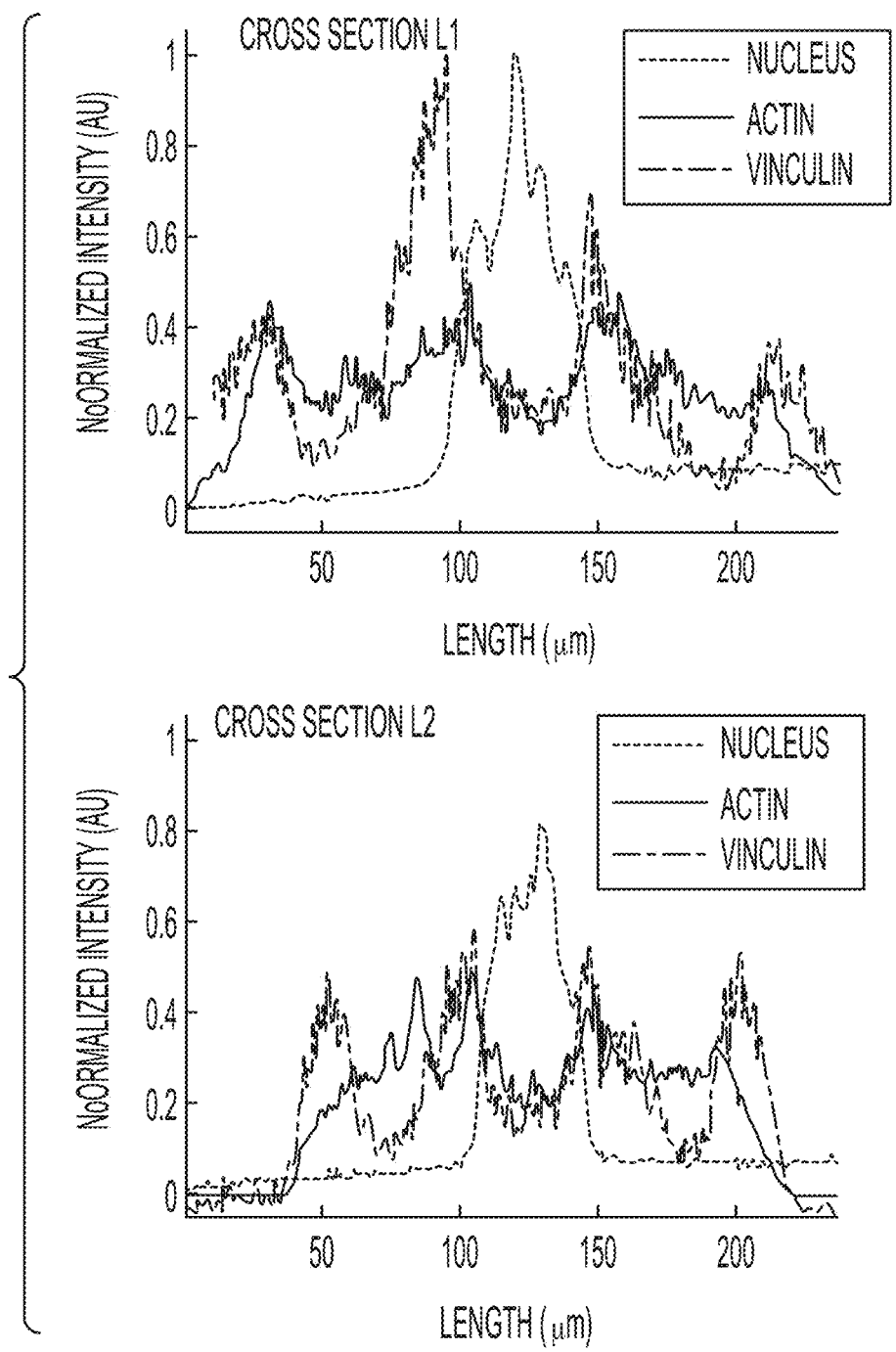
FIG. 6b shows cross sections of the fluorescence intensity as a function of position for the lines L1 and L2 that cut through the cell images in FIG. 6a. Fluorescent tags were separately applied to the cell nucleus, actin, and vinculin.

To further investigate the FA areas detected with PIS images, fluorescent images were acquired for cells imaged using PIS and PWS. In FIG. 6a, the top row shows the brightfield (BF), peak intensity shift (PIS), and peak wavelength shift (PWS) images, and the bottom row shows fluorescent images of the same cell with fluorescent tags applied to three different cellular components (actin, vinculin, and nucleus). FIG. 6b shows the fluorescence intensity as a function of position along the lines L1 and L2 shown in FIG. 6a for the nucleus, actin, and vinculin images. There is no obvious pattern similarity between the PIS image and actin (indicating the presence of cytoskeleton components) or nucleus images. However, the fluorescent image of vinculin (a type of FA molecule) in the bottom row of FIG. 6a indicates that the filopodia reside at the focal adhesion area along the stem cell boundary. As shown in FIG. 6a middle column, the PIS image shows a distribution pattern along the cell peripheral region that is similar to that in the vinculin image. As vinculin is an FA molecule, this similarity is further support that the PIS images show where FA areas are concentrated along the cell boundary. This data indicates that the high intensity areas in PIS images are co-localized with the FA areas. Therefore, the dimension change of the FA cluster can also be detected with PIS images using PROM.

Figure 7A:
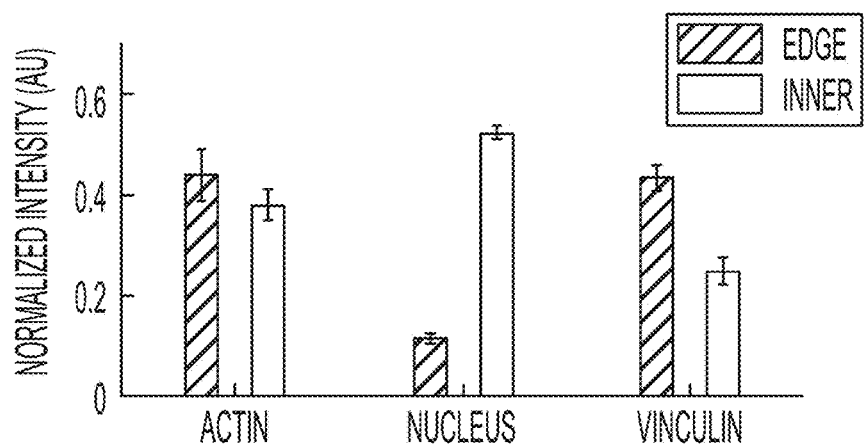
Figure 7B:
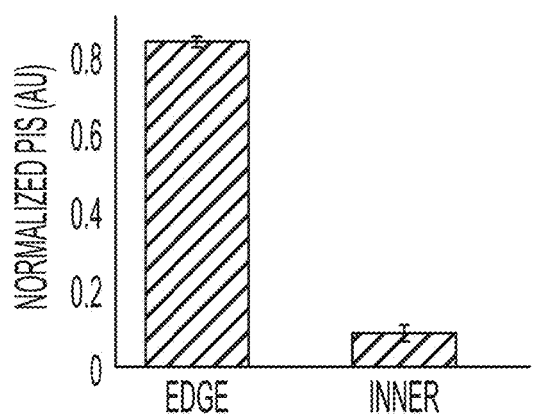
Figure 7C:
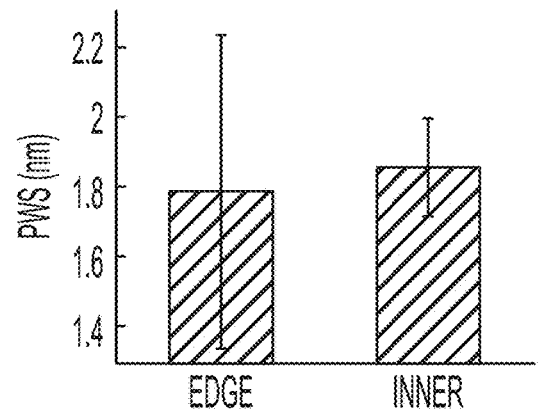

FIGS. 7a-c illustrate a statistical analysis for the fluorescent, PIS, and PWS images along the cell boundary (marked as "Edge") and within the nucleus area (marked as "Inner"). FIG. 7a is a bar graph that shows the data for the fluorescent images (including actin, nucleus, and vinculin). FIG. 7b is a bar graph that shows the data for the PIS images. FIG. 7c is a bar graph that shows the data in the PWS images.

The data in the bar graph of FIG. 7a demonstrate three different patterns of distribution along the cell edge and center. The nucleus image only shows high intensity within the area of the nucleus (because the fluorescent molecular probes tag nucleic acid material, such as chromosomes). Actin mainly functions as a cytoskeleton molecule that can rapidly remodel by dynamically forming microfilaments to support cell structure or participate in many important cellular processes, including cell division or cell signaling. As a scaffold protein, the distribution of actin is relatively uniform and thus the difference of fluorescent intensity between cell edge and center in the actin image is small. The vinculin is a membrane-cytoskeletal protein that is often localized in the FA area since it participates in linking between the transmembrane protein (e.g., integrin) and the cytoskeletal protein (e.g., actin). Therefore, the fluorescent dye for vinculin is often used to visualize the locations of FAs. The bar graph of FIG. 7a clearly shows that the distribution of vinculin is mainly along the cell periphery for a surface-attached cell. This distribution of vinculin is consistent with the distribution pattern of PIS indicated in the bar graph of FIG. 7b, which shows much a higher PIS at the edge of the cell than in the inner portion of the cell. On the other hand, the distribution of vinculin shown in FIG. 7a is not similar to the PWS data shown in the bar graph of FIG. 7c.

7. Other Applications

The data shown in FIG. 4a through FIG. 7c and discussed above demonstrates the utility of PROM for imaging cells and for particularly imaging portions of cells involved in FA formation. It is to be understood, however, that PROM has numerous other applications. For example, PROM may be used to detect viruses in a sample. A virus on the surface of the PC is capable of scattering light, resulting in a locally reduced reflected intensity. In general, any particle of a dielectric material, such as $TiO_2$ or $SiO_2$, on the surface of a PC is capable of outcoupling light from the PC, resulting in a locally reduced reflection intensity. The locations corresponding to viruses or other dielectric particles on the surface of the PC can be identified in a PROM image of the surface, and such locations can be counted to determine an abundance of such particles in the sample.

Further, the ability to count individual nanoparticles (50 nm to 500 nm in diameter) or microparticles (500 nm to 100 microns in diameter) of dielectric materials in a PROM image can be used to provide digital assays. For example, a dielectric nanoparticle or microparticle could be functionalized to specifically bind to an analyte, such as a protein, a nucleic acid sequence, or other biomolecule, and the surface of the PC can be functionalized to specifically bind to functionalized particles that have bound to the analyte. The functionalized PC surface can then be exposed to a sample that includes the analyte and the functionalized nanoparticles or microparticles and a PROM image obtained. The locations of locally reduced PIV in the resulting PROM image can be counted to determine how many analyte-bound particles have bound to the surface of the PC. This number can then be used to calculate an abundance of the analyte in the sample. This approach can be very useful for detecting biomolecules that are present in a sample in very low abundance, as individual biomolecules in the sample are counted by counting the dielectric nanoparticles or microparticles to which they are bound.

8. Conclusion

PROM is a novel label-free microscopy modality that can quantitatively measure the scatter-induced changes in reflected intensity from a photonic crystal biosensor surface to reveal the kinetic evolution and spatial features of focal adhesions that form at the cell-surface interface. Compared to a sensing approach in which image contrast is generated by the dielectric permittivity of attached cell components, PROM provides contrast in reflected resonant intensity that is induced by the refractive index contrast of localized protein clusters that occur at the cell-surface interface that comprise focal adhesion sites. Further, images of PIS and PWS may be gathered from the same spectral information for the same cells. The two imaging modalities can reveal distinct spatial patterns, and thus provide complementary information about cell-surface activity. Dynamic images of PIS and PWS can be gathered over extended time periods, with ~10 second temporal resolution via a line-scanning approach to generate time-course movies of cell-surface behavior during processes that occur over several hours. As a label-free imaging approach, PROM does not suffer from the limitations of fluorescence-based microscopy, which include photobleaching and stain cytotoxicity. For example, PROM can be used to acquire dynamic PIS images of live cell adhesion over extended time periods that may not feasible for fluorescence imaging due to photobleaching. Thus, PROM is shown to be a highly useful tool that can reveal the mechanisms of biological processes that occur near the cell membrane, for example, when the cell is attached to extracellular matrix materials during apoptosis, stem cell differentiation, migration, division, and metastasis.

What is claimed is:

1. An instrument for photonic resonator outcoupler microscopy (PROM) of a sample on a surface of a photonic crystal, the instrument comprising:
   a light source configured to emit incident light;
   an optical system configured to focus the incident light to provide focused light that sequentially illuminates each linear region of a plurality of linear regions of the surface of the photonic crystal;
   a spectrometer, wherein the spectrometer is configured to (i) receive reflected light that has reflected from each linear region of the surface of the photonic crystal in response to illumination by the focused light and (ii) for each linear region, spectrally disperse the reflected light from the linear region into a set of spectra, wherein each spectrum in the set of spectra corresponds to a respective location in the linear region;
   a camera optically coupled to the spectrometer, wherein the camera is configured to acquire a plurality of images, wherein each image corresponds to a particular linear region of the plurality of linear regions and records the set of spectra of the particular linear region; and
   an analysis system, wherein the analysis system is configured to (i) analyze the acquired images to identify for each location in each linear region of the surface of the photonic crystal, a respective resonant wavelength in the spectrum for the location and a respective intensity value of the respective resonant wavelength, so as to obtain a plurality of intensity values, and (ii) generate a PROM image of the sample based on the plurality of intensity values, wherein different intensity values in the PROM image are indicative of different amounts of resonant wavelength scattering by components of the sample at different locations.

2. The instrument of claim 1, wherein the photonic crystal has a range of resonant wavelengths based on different components of the sample being proximate to different locations of the surface of the photonic crystal, and wherein the incident light emitted by the light source has a range of wavelengths that includes the range of resonant wavelengths.

3. The instrument of claim 2, wherein the light source comprises a light emitting diode (LED).

4. The instrument of claim 1, wherein the sample comprises a cell, wherein different portions of the cell are proximate to different locations of the surface of the photonic crystal and result in different intensity values in the PROM image of the sample.

5. The instrument of claim 1, further comprising a motorized stage configured to move the photonic crystal relative to the optical system.

6. The instrument of claim 5, wherein the photonic crystal has an upper surface and a lower surface, wherein the sample is on the upper surface of the photonic crystal, wherein the motorized stage is configured to support the lower surface of the photonic crystal, and wherein the optical system is configured to illuminate the photonic crystal through the lower surface.

7. The instrument of claim 1, wherein the optical system comprises a cylindrical lens and an objective lens, wherein the cylindrical lens is configured to focus the incident light to a line at a focal plane of the objective lens.

8. The instrument of claim 7, wherein the spectrometer comprises an entrance slit, wherein the entrance slit is optically to the objective lens.

9. The instrument of claim 1, wherein the photonic crystal comprises a grating structure having a grating direction, and wherein the focused light comprises a focal line on the surface of the photonic crystal such that the focal lines is substantially perpendicular to the grating direction.

10. The instrument of claim 9, further comprising a polarizer, wherein the polarizer is configured to linearly polarize the incident light such that electric field vectors of the focused light illuminating the photonic crystal are oriented perpendicular to the grating structure.

11. The instrument of claim 1, wherein the instrument is configured to generate a plurality of PROM images of the sample over a period of time.

12. The instrument of claim 1, wherein the camera comprises a two-dimensional array of light sensitive elements, wherein in an image acquired for a linear region of the surface of the photonic crystal each light sensitive element receives light in a particular range of wavelengths corresponding to a portion of the spectrum of a particular location in the linear region.

13. The instrument of claim 12, wherein the two-dimensional array of light sensitive elements comprises a charge coupled device (CCD).

14. The instrument of claim 1, wherein the analysis system is further configured to:
   for each resonant wavelength, determine a respective wavelength shift as a difference between the resonant wavelength and a reference wavelength, so as to obtain a plurality of wavelength shifts; and
   generate a peak wavelength shift (PWS) image of the sample based on the plurality of wavelength shifts.

15. A method for photonic resonator outcoupler microscopy (PROM) of a sample on a surface of a photonic crystal, the method comprising:
   emitting incident light from a light source;
   focusing the incident light, by an optical system, to provide focused light;
   sequentially illuminating with the focused light each linear region of a plurality of linear regions of the surface of the photonic crystal;

receiving, by a spectrometer, reflected light that has reflected from each linear region of the surface of the photonic crystal in response to illumination by the focused light;

for each linear region, spectrally dispersing, by the spectrometer, the reflected light from the linear region into a set of spectra, wherein each spectrum in the set of spectra corresponds to a respective location in the linear region;

acquiring, by a camera optically coupled to the spectrometer, a plurality of images, wherein each image corresponds to a particular linear region of the plurality of linear regions and records the set of spectra of the particular linear region;

analyzing the acquired images to identify for each location in each linear region of the surface of the photonic crystal a respective resonant wavelength in the spectrum for the location and a respective intensity value of the respective resonant wavelength, so as to obtain a plurality of resonant wavelengths and a plurality of intensity values; and generating a PROM image of the sample based on the plurality of intensity values, wherein different intensity values in the PROM image are indicative of different amounts of resonant wavelength scattering by components of the sample at different locations.

16. The method of claim 15, wherein the photonic crystal has an upper surface and a lower surface, wherein the sample is on the upper surface of the photonic crystal, and wherein the upper surface of the photonic crystal is illuminated through the lower surface.

17. The method of claim 16, wherein the lower surface of the photonic crystal is supported by a motorized stage, and wherein sequentially illuminating with the focused light each linear region of a plurality of linear regions of the surface of the photonic crystal comprises:

using the motorized stage to move the photonic crystal relative to the optical system.

18. The method of claim 15, wherein analyzing the acquired images to identify for each location in each linear region of the surface of the photonic crystal a respective resonant wavelength in the spectrum for the location comprises:

identifying a peak wavelength in the spectrum for the location as the location's respective resonant wavelength.

19. The method of claim 18, wherein generating the PROM image of the sample based on the plurality of intensity values comprises:

for each intensity value of the plurality of intensity values, determining a respective intensity shift as a difference between the intensity value and a reference intensity value, so as to obtain a plurality of intensity shifts; and generating the PROM image based on the plurality of intensity shifts.

20. The method of claim 19, further comprising:

for each resonant wavelength of the plurality of resonant wavelengths, determining a respective wavelength shift as a difference between the resonant wavelength and a reference wavelength, so as to obtain a plurality of wavelength shifts; and generating a peak wavelength shift (PWS) image of the sample based on the plurality of wavelength shifts.

* * * * *